US012576061B2

(12) United States Patent
Hirano

(10) Patent No.: US 12,576,061 B2
(45) Date of Patent: Mar. 17, 2026

(54) AGENT FOR INDUCING REGRESSION OF TRIGLYCERIDE DEPOSIT ATHEROSCLEROSIS

(71) Applicant: OSAKA UNIVERSITY, Osaka (JP)

(72) Inventor: Ken-ichi Hirano, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 560 days.

(21) Appl. No.: 17/926,301

(22) PCT Filed: Mar. 5, 2021

(86) PCT No.: PCT/JP2021/008689
§ 371 (c)(1),
(2) Date: Nov. 18, 2022

(87) PCT Pub. No.: WO2021/235044
PCT Pub. Date: Nov. 25, 2021

(65) Prior Publication Data
US 2023/0210805 A1 Jul. 6, 2023

(30) Foreign Application Priority Data

May 22, 2020 (JP) ................................. 2020-090091
Nov. 18, 2020 (JP) ................................. 2020-192099

(51) Int. Cl.
*A61K 31/225* (2006.01)
*A61P 9/10* (2006.01)

(52) U.S. Cl.
CPC .............. *A61K 31/225* (2013.01); *A61P 9/10* (2018.01)

(58) Field of Classification Search
CPC ......... A61K 31/225; A61K 31/23; A61P 9/10; A61P 9/00; A23L 33/12; A23L 2/52
See application file for complete search history.

(56) References Cited

U.S. PATENT DOCUMENTS

2014/0296338 A1* 10/2014 Hirano ................... A61K 31/19
514/547

FOREIGN PATENT DOCUMENTS

JP        5810166        11/2015
WO    2013/031729        3/2013

OTHER PUBLICATIONS

International Search Report issued Apr. 20, 2021 in International (PCT) Application No. PCT/JP2021/008689.
Akira Suzuki et al., "Tricaprin Rescues Myocardial Abnormality in a Mouse Model of Triglyceride Deposit Cardiomyovasculopathy", Journal of Oleo Science, vol. 67 (8), pp. 983-989 (pp. 1-7), 2018, cited in ISR and CF.

(Continued)

*Primary Examiner* — Deborah D Carr
(74) *Attorney, Agent, or Firm* — Wenderoth, Lind & Ponack, L.L.P.

(57) ABSTRACT
The present invention provides an agent for inducing regression of triglyceride (TG) deposit atherosclerosis, which agent comprises tricaprin/trisdecanoin as an active ingredient, an agent for improving blood flow in a patient with TG deposit atherosclerosis, which agent comprises tricaprin/trisdecanoin as an active ingredient, and a pharmaceutical or food or drink product comprising the agent for inducing regression of TG deposit atherosclerosis or the agent for improving blood flow.

8 Claims, 6 Drawing Sheets

(56) References Cited

OTHER PUBLICATIONS

Rojeet Shrestha et al., "Change in Plasma Total, Esterified and Non-esterified Capric Acid Concentrations during a Short-Term Oral Administration of Synthetic Tricaprin in Dogs", Analytical Sciences, vol. 33, pp. 1297-1303, Nov. 2017, cited in ISR.

Stephen J. Nicholls et al., "Effect of Evolocumab on Progression of Coronary Disease in Statin-Treated Patients The GLAGOV Randomized Clinical Trial", JAMA Original Investigation, 316(22), pp. 2373-2384, 2016, cited in the specification.

Decision of Refusal issued May 10, 2022 in corresponding Japanese Application No. 2022-514027, together with machine English translation thereof.

Office Action (Notice of Reasons for Refusal) issued Mar. 29, 2022 in corresponding Japanese Application No. 2022-514027, together with machine English translation thereof.

Ming Li et al., "Triglyceride deposit cardiomyovasculopathy: a rare cardiovascular disorder", Orphanet Journal of Rare Diseases, 14:134, pp. 1-9, 2019, cited in CF.

International Preliminary Report on Patentability and Written Opinion of the International Searching Authority issued Nov. 17, 2022 in International (PCT) Application No. PCT/JP2021/008689.

Office Action issued Mar. 11, 2025 in corresponding Japanese Application No. 2022-127299, with English machine translation.

"New Date Determination: 10 years of research on triglyceride accumulation myocardial vasculopathy (TGCV) and future prospects", Osaka University Graduate School Medicine System Graduate Course and Medical Department, (2019), pp. 1-6.

"Development of a pharmaceutical product containing medium-chain fatty acids against triglyceride accumulation, 2012 Summary/Distributed Research Report", (2014), pp. 1-21.

"Development of a medicine containing medium-chain fatty acids against neutral fat storage myocardium", (2014), pp. 1-4.

"Triglyceride and blood vessels", Journal of the Japanese Association for Cerebro-cardiovascular Disease Control, (1996), vol. 30, No. 3, pp. 236-242.

Office Action issued Dec. 5, 2023 in corresponding Japanese Patent Application No. 2022-514027, with English machine translation.

Extended European Search Report issued May 2, 2024 in corresponding European Patent Application No. EP 21809755.8.

* cited by examiner

AGENT FOR INDUCING REGRESSION OF TRIGLYCERIDE DEPOSIT ATHEROSCLEROSIS

TECHNICAL FIELD

The present invention relates to an agent for inducing regression of triglyceride deposit atherosclerosis.

BACKGROUND ART

Administration of statins (HMG-CoA reductase inhibitors) for lowering LDL cholesterol levels is the basis of atherosclerosis treatment. A number of studies have suggested a correlation between lowering LDL cholesterol levels and reducing the incidence of major adverse cardiovascular events. Proprotein convertase subtilisin kexin type 9 (PCSK9) is known to inhibit cellular LDL cholesterol uptake into cells by promoting degradation of LDL receptors. Therefore, administration of PCSK9 inhibitors, such as monoclonal antibodies against PCSK9, alone or in combination with statins, can lower LDL cholesterol levels.

Non-patent literature 1 describes a multicenter, double-blind, placebo-controlled, randomized clinical trial in which 968 patients who had coronary artery stenosis confirmed by coronary angiography and were undergoing statin treatment were randomly assigned to receive evolocumab (monoclonal antibody against PCSK9) (484 patients) or placebo (484 patients). LDL cholesterol levels and percent atheroma volume (PVA) in the patients at week 76 were evaluated to determine efficacy in this trial. The results show that the LDL cholesterol level and atheroma volume at week 76 remained unchanged from those before the start of the trial in the placebo group. On the other hand, in the evolocumab group, the LDL cholesterol level was reduced at week 76 to about 40% of the level before the start of the trial (from 92.6 mg/dL to 36.6 mg/dL), while the percent atheroma volume was reduced by only 0.95% at week 76. That is, atheroma volume hardly decreased although LDL cholesterol levels decreased. As seen from these results, no medicine or therapy has yet been developed to induce atherosclerotic plaque regression.

The present inventor previously found that medium-chain triglycerides are effective in the treatment of triglyceride deposit cardiovascular diseases in diabetic patients and obtained a patent for this invention (Patent Literature 1).

CITATION LIST

Patent Literature

Patent Literature 1: Japanese Patent No. 5810166

Non-Patent Literature

Non-Patent Literature 1:
JAMA. 2016; 316(22):2373-2384. doi:10.1001/jama.2016.16951

SUMMARY OF INVENTION

Technical Problem

An object of the present invention is to provide an agent for inducing regression of triglyceride (TG) deposit atherosclerosis and an agent for improving blood flow in a patient having TG deposit atherosclerosis.

Solution to Problem

The present invention includes the following to achieve the above-mentioned objects.

[1] An agent for inducing regression of triglyceride deposit atherosclerosis, comprising tricaprin/trisdecanoin as an active ingredient.

[2] The agent for inducing regression of triglyceride deposit atherosclerosis according to the above [1], wherein the agent is for a patient with refractory atherosclerosis.

[3] The agent for inducing regression of triglyceride deposit atherosclerosis according to the above [1], wherein the agent is for an atherosclerotic patient having diabetes or chronic kidney disease, or for an atherosclerotic patient undergoing hemodialysis.

[4] The agent for inducing regression of triglyceride deposit atherosclerosis according to any one of the above [1] to [3], wherein the agent is administered in a daily dose containing 1.5 g to 9.0 g of the active ingredient for at least 50 days.

[5] An agent for improving blood flow in a patient with triglyceride deposit atherosclerosis, comprising tricaprin/trisdecanoin as an active ingredient.

[6] The agent for improving blood flow according to the above [5], wherein the patient with triglyceride deposit atherosclerosis is a patient with refractory atherosclerosis.

[7] The agent for improving blood flow according to the above [5], wherein the patient with triglyceride deposit atherosclerosis is a patient having diabetes or chronic kidney disease, or a patient undergoing hemodialysis.

[8] A pharmaceutical product comprising the agent for inducing regression of triglyceride deposit atherosclerosis according to any one of the above [1] to [4] or the agent for improving blood flow according to any one of the above [5] to [7].

[9] A food or drink product comprising the agent for inducing regression of triglyceride deposit atherosclerosis according to any one of the above [1] to [4] or the agent for improving blood flow according to any one of the above [5] to [7].

Advantageous Effects of Invention

The present invention provides an agent for inducing regression of triglyceride (TG) deposit atherosclerosis and an agent for improving blood flow in a patient having TG deposit atherosclerosis. The present invention enables regression of TG deposit atherosclerosis and improvement of blood flow.

DESCRIPTION OF EMBODIMENTS

Figure 1:
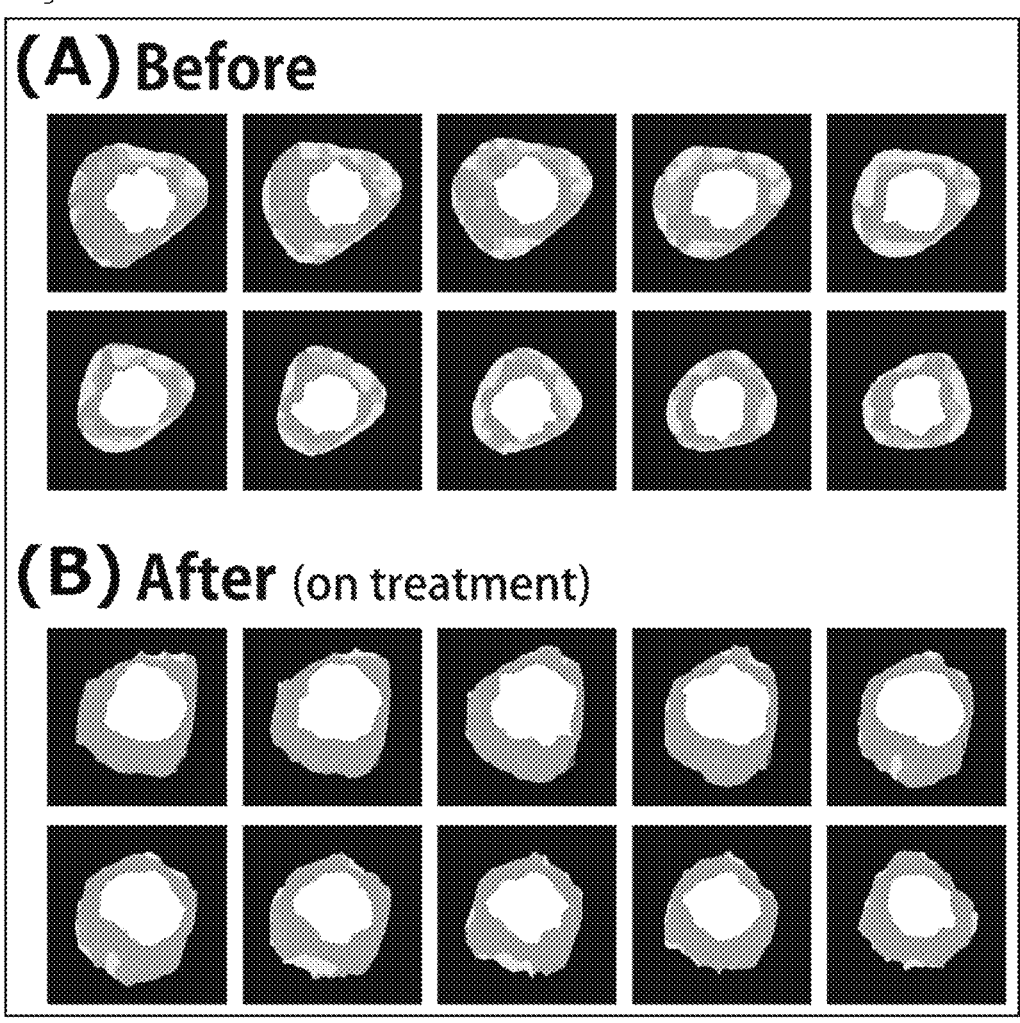
FIG. 1 shows cross-sectional images of the coronary artery in the patient in Example 1 to examine lipid accumulation in the coronary artery before and after a 50-day tricaprin/trisdecanoin diet. The results before the start of the tricaprin/trisdecanoin diet (A) and 50 days after the start of the tricaprin/trisdecanoin diet (B) are shown.

The present invention provides an agent for inducing regression of triglyceride (TG) deposit atherosclerosis, which agent comprises tricaprin/trisdecanoin as an active ingredient (hereinafter referred to as "the regression inducing agent of the present invention"). The active ingredient, tricaprin/trisdecanoin, is a triacylglycerol consisting of a glycerol molecule bound to three molecules of capric acid (decanoic acid) via ester bonds. The form of tricaprin/trisdecanoin is not limited and may be in a liquid, solid, or powder form.

The tricaprin/trisdecanoin can be produced by known methods. For example, the tricaprin/trisdecanoin can be produced by dehydration-condensation of capric acid and glycerol in the presence of a catalyst, preferably in the absence of a catalyst, at 50 to 250° C., more preferably 120° C. to 180° C., preferably at a reduced pressure. The catalyst is not particularly limited, and for example, acid or base catalysts commonly used for ester exchange can be used.

The subject to be treated with the regression inducing agent of the present invention is a patient who has been diagnosed with suspected atherosclerosis by a physician. Atherosclerotic patients are thought to have a combination of cholesterol deposit atherosclerosis and TG deposit atherosclerosis at various ratios. In general, patients with a high ratio of cholesterol deposit atherosclerosis have symptom improvement after cholesterol-lowering treatment with statins, etc., whereas patients with a high ratio of TG deposit atherosclerosis have no symptom improvement even when their cholesterol levels are lowered. In the present invention, the subject to be treated with the regression inducing agent of the present invention may be any patient who has been diagnosed with suspected atherosclerosis by a physician, and no confirmation of TG deposit atherosclerosis is required.

The subject to be treated with the regression inducing agent of the present invention may be a patient with confirmed TG deposit atherosclerosis. The patient with confirmed TG deposit atherosclerosis may be a patient with triglyceride deposit cardiomyovasculopathy (TGCV). TGCV is an intractable disease caused by TG accumulation in cardiomyocytes and coronary atherosclerotic plaques, resulting in severe heart failure and arrhythmia (Hirano K, et al. N Engl J Med. 2008). The diagnosis of TG deposit atherosclerosis can be made, for example, by computed tomography angiography showing lipid deposition protruding from the adventitial side toward the medial side in a nodular, peninsular or bridging pattern (which is regarded as the characteristic pattern of TG deposit atherosclerosis (see Reference 1: Annals of Nuclear Cardiology, 2017 Volume 3 Issue 1 Pages 94-102, Reference 2: Diabetes Care, 2019 Volume 42, Pages 983-986).

The vessel in which TG deposit atherosclerosis can develop is not limited, and examples of such a vessel include blood vessels of the heart, brain, upper and lower limbs, and kidneys, and mesenteric arteries. Diseases caused by TG deposit atherosclerosis include, but are not limited to, angina, myocardial infarction, heart failure, cardiac hypertrophy, hypertension, stroke, cerebral infarction, cerebral hemorrhage, subarachnoid hemorrhage, transient cerebral ischemia, atherosclerosis, arteriosclerosis obliterans, renal artery stenosis, mesenteric artery occlusion, and aortic aneurysm rupture. That is, patients with these diseases are the subjects to be treated with the regression inducing agent of the present invention.

Patients in whom TG deposit atherosclerosis can develop include patients with adipose triglyceride lipase (ATGL) deficiency. In addition, the patients in whom TG deposit atherosclerosis can develop include patients with refractory atherosclerosis. The term "patients with refractory atherosclerosis" as used herein means patients who show resistance to standard atherosclerosis therapies. The standard atherosclerosis therapies include, for example, catheter intervention, serum lipid control, and blood glucose control. For serum lipid control, statins, fibrates, fish oils such as EPA, and other drugs are administered. For blood glucose control, insulin preparations, DPP-4 inhibitors, SGLT2 inhibitors, biguanides, and other drugs are administered. More specifically, the "patients with refractory atherosclerosis" include atherosclerotic patients who have no symptom improvement after intravascular stent placement, patients who have no symptom improvement while serum lipid levels are controlled within the normal range, and patients who have no symptom improvement while blood glucose levels are controlled within the normal range. That is, the regression inducing agent of the present invention is very useful for patients with refractory atherosclerosis.

TG deposit atherosclerosis can develop also in patients diagnosed with diabetes (type 1 or 2 diabetes), hyperlipidemia, hypercholesterolemia, hypertension, obesity, liver disease, kidney disease, and other diseases. That is, the regression inducing agent of the present invention is useful as an agent of choice for patients who have such diseases and have been diagnosed with suspected atherosclerosis.

Furthermore, atherosclerotic patients having chronic kidney disease and atherosclerotic patients undergoing hemodialysis are known to be less responsive to statins and more likely to have TG deposit atherosclerosis. Such patients can benefit from treatment with the regression inducing agent of the present invention.

As used herein, "regression of TG deposit atherosclerosis" means that diminishment or disappearance of the characteristic pattern of TG deposit atherosclerosis described above, which is accompanied by opening of the vascular lumen, and improvement or reduction in the degree of stenosis. The TG deposit pattern in the vessels can be assessed by image analysis based on computed tomography (CT) angiography, intravascular ultrasound (IVUS), optical coherence tomography (OCT), cardiac magnetic resonance imaging (MRI), coronary angiography, coronary biopsy (Rotablator), carotid echocardiography, etc.

The present inventor confirmed that 3-month oral tricaprin/trisdecanoin treatment in a refractory angina patient with a newly diagnosed idiopathic TGCV resulted in improvement in coronary blood flow. That is, the present invention provides an agent for improving blood flow in a patient with TG deposit atherosclerosis, which agent comprises tricaprin/trisdecanoin as an active ingredient (hereinafter referred to as "the blood flow improving agent of the present invention"). The patient to be treated with the blood flow improving agent of the present invention is the same as the patient to be treated with the regression inducing agent of the present invention described above.

The regression inducing agent or blood flow improving agent of the present invention can be embodied in the form of a pharmaceutical product. When the regression inducing agent or blood flow improving agent of the present invention is embodied in the form of a pharmaceutical product, tricaprin/trisdecanoin can be formulated into a dosage form according to conventional methods. For example, the dosage form can be an oral preparation, and examples of the oral preparation include solid or liquid preparations, specifically tablets (including sugar-coated tablets and film-coated tablets), pills, granules, powders, capsules (including soft capsules), syrups, emulsions, suspensions, etc. These preparations can be produced by known methods and contain one or more carriers, diluents or excipients commonly used in the field of pharmaceutical formulation. For example, carriers or excipients used for tablets include lactose, starch, sucrose, and magnesium stearate. The dosage form may be a parenteral preparation, and examples of the parenteral preparation include injections and suppositories. The injections include an intravenous injection, a subcutaneous injection, an intracutaneous injection, an intramuscular injection, an intravenous infusion, and an intraarticular injection. These injections are prepared according to known methods, for example, by dissolving, suspending or emulsifying the active ingredient in a sterile aqueous or oily liquid commonly used for injections. As an aqueous liquid for injection, for example, physiological saline, an isotonic solution containing glucose and an auxiliary substance, or the like can be used, optionally together with a suitable solubilizer such as alcohols (e.g., ethanol, etc.), polyalcohols (e.g., propylene glycol, polyethylene glycol, etc.), and nonionic surfactants (e.g., polysorbate 80, HCO-50, etc.). As an oily liquid, for example, sesame oil, soybean oil, or the like can be used, optionally together with a solubilizer such as benzyl benzoate and benzyl alcohol. Suppositories for rectal administration are prepared by mixing the active ingredient with a base commonly used for suppositories. The pharmaceutical preparation that can be obtained in the above manner is safe and less toxic, and therefore can be orally or parenterally administered to, for example, humans and other mammals. Preferably, it is orally administered.

The regression inducing agent or blood flow improving agent of the present invention can be embodied in the form of a food or drink product. Examples of the food or drink product include foods with functional claims, foods for specified health uses, foods for medical uses, foods for special dietary uses, nutritionally fortified foods, health foods, health supplements, and dietary supplements. The form of the food or drink is not particularly limited. Exemplary forms include tablets, granules, powders, drinkable preparations, etc.; drinks such as tea drink, soft drink, carbonated drink, nutritional drink, fruit juice, and lactic acid drink; confectioneries such as hard candy, candy, gum, chocolate, snack, biscuit, jelly, jam, cream, and baked confectioneries, and breads; processed seafood or livestock products such as fish cake, ham, and sausage; dairy products such as processed milk and fermented milk; fats, oils and processed fat and oil products such as vegetable oil, tempura oil, margarine, mayonnaise, shortening, whipped cream, and dressing; seasonings such as sauce and tare sauce; retort food products such as curry, stew, rice bowl, rice porridge, and rice soup; and cold confectioneries such as ice cream, sherbet, and shaved ice.

The dosage of the regression inducing agent or blood flow improving agent of the present invention in humans can be selected according to the patient's age, sex, weight, and severity of disease. The dosage of the active ingredient, tricaprin/trisdecanoin, is usually selected from the range of 0.1 g to 50 g per day, may be 0.2 g, 0.4 g, 0.6 g, 0.8 g, 1.0 g, 1.1 g, 1.2 g, 1.3 g, 1.4 g, 1.5 g, or more per day, and may be 45 g, 40 g, 35 g, 30 g, 25 g, 20 g, 15 g, 10 g, 9.0 g, or less per day. Preferably, the dosage of tricaprin/trisdecanoin is selected from the range of 1.0 g to 10.0 g, more preferably 1.5 g to 9.0 g. The frequency of administration per day may be once daily or several times daily.

The period of administration of the regression inducing agent or blood flow improving agent of the present invention is not particularly limited. For example, the end point of the period of administration can be determined from periodical assessment of regression of TG deposit atherosclerosis or improvement of blood flow. The agent is preferably administered for at least 50 days. The period of administration may be 2 months or more, 3 months or more, 4 months or more, 5 months or more, 6 months or more, 7 months or more, 8 months or more, 9 months or more, 10 months or more, or 11 months or more, or 1 year or more.

The present invention includes the following.

(a1) A method for inducing regression of triglyceride deposit atherosclerosis, comprising administering an effective amount of tricaprin/trisdecanoin to a mammal.

(a2) A method for improving blood flow in a patient with triglyceride deposit atherosclerosis, comprising administering an effective amount of tricaprin/trisdecanoin to a mammal.

(b1-1) Tricaprin/trisdecanoin for use in inducing regression of triglyceride deposit atherosclerosis.

(b1-2) Use of tricaprin/trisdecanoin for a food or drink product for inducing regression of triglyceride deposit atherosclerosis.

(b2-1) Tricaprin/trisdecanoin for use in improving blood flow in a patient with triglyceride deposit atherosclerosis.

(b2-2) Use of tricaprin/trisdecanoin for a food or drink product for improving blood flow in a patient with triglyceride deposit atherosclerosis.

(c1) Use of tricaprin/trisdecanoin for production of an agent for inducing regression of triglyceride deposit atherosclerosis.

(c2) Use of tricaprin/trisdecanoin for production of an agent for improving blood flow in a patient with triglyceride deposit atherosclerosis.

EXAMPLES

Hereinafter, the present invention will be described in detail by examples, but the present invention is not limited thereto.

Example 1

(1) Patient

A 44-year-old woman with genetic adipose triglyceride lipase (ATGL) deficiency. Coronary CT angiography revealed TG deposit atherosclerosis, and the patient was started on a tricaprin/trisdecanoin diet. The patient received tricaprin/trisdecanoin three times per day after meals in a total daily dose of 6 to 9 g for 50 days.

(2) Assessment of Lipid Accumulation in the Coronary Artery

Before and 50 days after the start of the tricaprin/trisdecanoin diet, a standard coronary CT angiography was performed to generate three-dimensional (3D) DICOM images of the left anterior descending coronary artery. The images were resampled to a voxel size of $0.1 \text{ mm}^3$ and color-coded according to CT values of individual voxels. Smoothing was applied between adjacent voxels. Colors were coded as follows: light gray (yellow in the color image): −25 HU to 0 HU (massive lipid accumulation); medium gray (orange in the color image): 0 HU to 40 HU (moderate lipid accumulation); dark gray (green in the color image): 40 HU to 125 HU (no lipid accumulation).

(3) Results

Color-coded cross-sectional images of the coronary artery are shown in FIG. 1. The results before the start of the tricaprin/trisdecanoin diet (A) and 50 days after the start of the tricaprin/trisdecanoin diet (B) are shown. The results showed that the 50-day tricaprin/trisdecanoin diet resulted in regression of TG deposit atherosclerosis in the coronary artery.

Example 2

(1) Patient

A 65-year-old man who had suffered from refractory angina for years. The patient had diabetes with a history of middle cerebral artery occlusion and cerebral infarction. The patient presented to hospital with a chief complaint of rest and nocturnal angina. Coronary CT angiography revealed diffuse coronary atherosclerosis. His chest pain was refractory to existing medications (sublingual nitroglycerin, calcium channel blockers, β-blockers, antiplatelet agents, and statins) and rather worsened. Coronary CT angiography revealed TG deposit atherosclerosis, and the patient was started on a tricaprin/trisdecanoin diet. The patient received tricaprin/trisdecanoin three times per day after meals in a total daily dose of 1.5 g for 4 years. The patient was free from recurrent cerebral infarction.

(2) Assessment of Lipid Accumulation in the Coronary Artery

Before and 4 years after the start of the tricaprin/trisdecanoin diet, a standard coronary CT angiography was performed, and the images of the inside of the left anterior descending coronary artery were color-coded in the same manner as described in Example 1. The images of the designated segment of the coronary artery were analyzed with a 3D image analysis system SYNAPSE VINCENT v5.5 (FUJIFILM Corporation) to examine changes in lipid accumulation and vascular lumen size in the designated segment. In the image analysis, the area with CT values ranging −25 to 40 HU was regarded as lipid accumulation, and the area with CT values ranging 215 to 700 HU was regarded as the vascular lumen.

Figure 2:
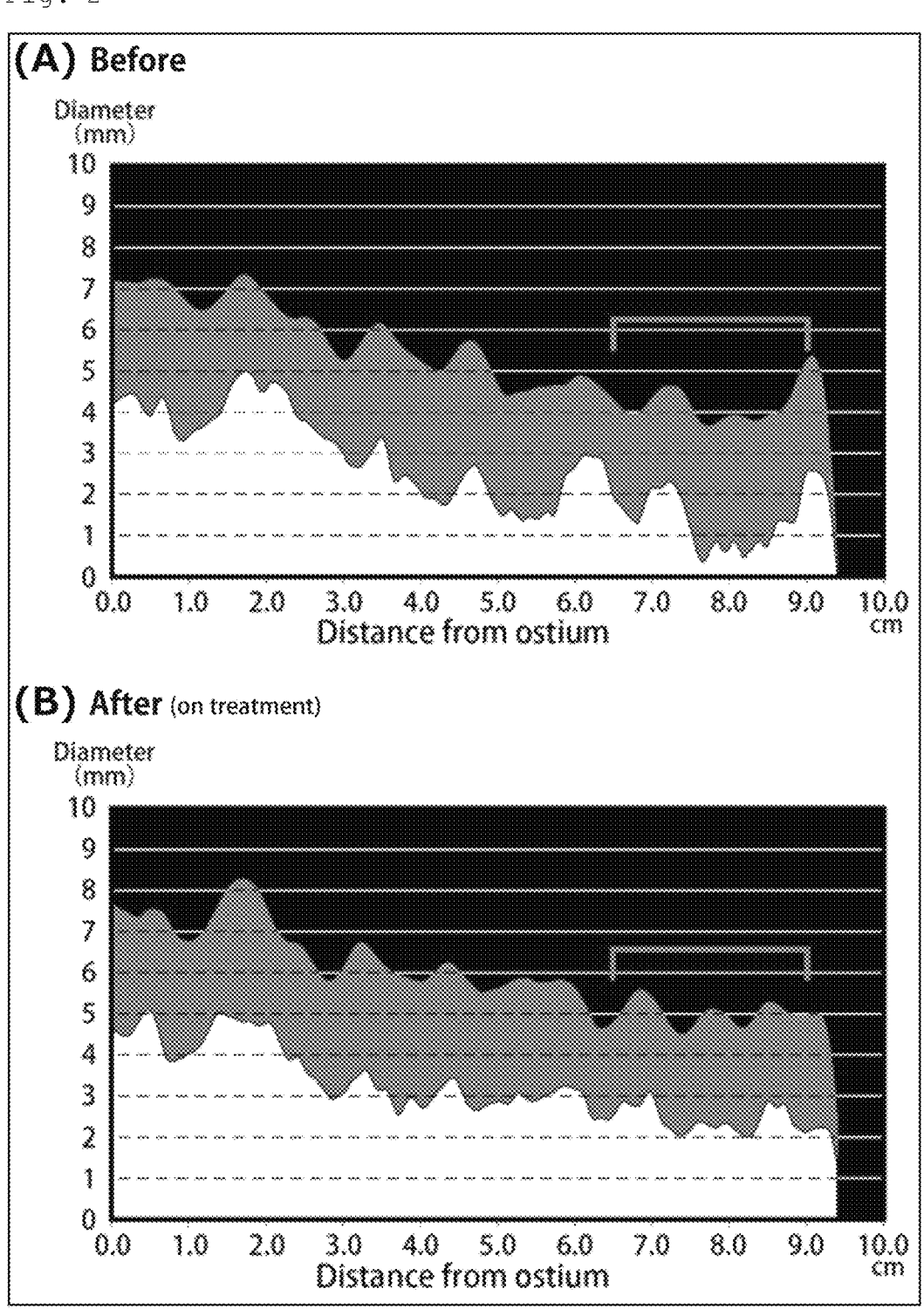
FIG. 2 shows a plot of the artery diameter against the distance from the coronary artery ostium in the patient in Example 2 to examine lipid accumulation in the coronary artery before and after a 4-year tricaprin/trisdecanoin diet. The results before the start of the tricaprin/trisdecanoin diet (A) and 4 years after the start of the tricaprin/trisdecanoin diet (B) are shown.
Figure 3:
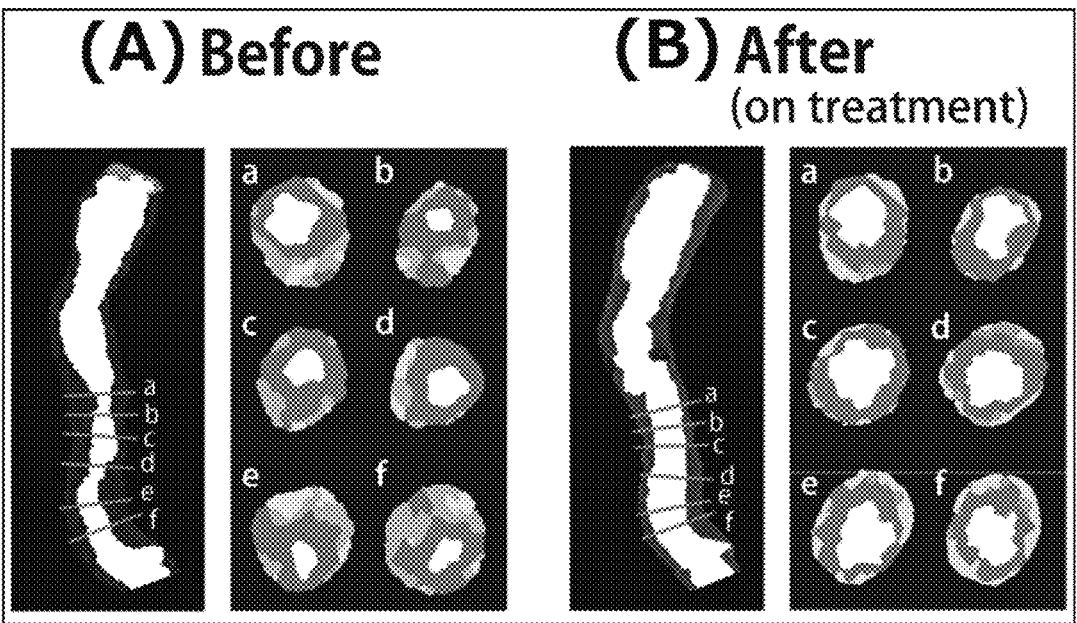
FIG. 3 shows cross-sectional images of the coronary artery in the patient in Example 2 to examine lipid accumulation in the coronary artery before and after a 4-year tricaprin/trisdecanoin diet. The results before the start of the tricaprin/trisdecanoin diet (A) and 4 years after the start of the tricaprin/trisdecanoin diet (B) are shown.

The results are shown in FIGS. 2 and 3. In FIG. 2, the horizontal axis is the distance from the coronary artery ostium, and the vertical axis is the diameter of the artery. The results before the start of the tricaprin/trisdecanoin diet (A) and 4 years after the start of the tricaprin/trisdecanoin diet (B) are shown. The white area represents a blood flow area, and the gray (blue in the color image) area represents a triglyceride layer. FIG. 3 shows color-coded cross-sectional images of the coronary artery at six positions (a to f) in a segment 6.5 to 9.0 cm away from the coronary artery ostium. Before the start of the diet, 90% to 75% diffuse stenosis was observed in the segment 7 to 9 cm away from the coronary artery ostium (FIG. 2A). In the same segment, lipid deposition protruded from the adventitial side toward the medial side in a nodular, peninsular or bridging pattern (FIG. 3A). This characteristic pattern of TG deposit atherosclerosis diminished or disappeared after treatment (FIG. 2B), and the stenosis of the vascular lumen was clearly improved to an extent of about 25% stenosis (FIG. 3B). The results of the 3D image analysis are shown in Table 1. As shown in FIGS. 2 and 3 and Table 1, the 4-year tricaprin/trisdecanoin diet resulted in regression of TG deposit atherosclerosis in the coronary artery and a marked enlargement of the diameter of the vascular lumen through which the blood flowed.

TABLE 1

| Segment | Lipid accumulation | Vascular lumen |
|---|---|---|
| Designated in FIG. 2 2.2 cm | 27% reduction | 260% increase |

(3) Changes in Serum Lipid Levels Before and After the Start of the Tricaprin/Trisdecanoin Diet The mean values of the triglyceride, LDL cholesterol, and HDL cholesterol levels measured before the start of the tricaprin/trisdecanoin diet were compared to those measured for 4 years after the start of the tricaprin/trisdecanoin diet. The results are shown in Table 2. The serum lipid levels after the start of the tricaprin/trisdecanoin diet remained almost unchanged from those before the start of the diet, indicating that tricaprin/trisdecanoin diet had no effect on the serum lipid levels in the patient. The LDL cholesterol level was under control within the normal range (60 to 119 mg/dL).

TABLE 2

| Example 2 | Before treatment (Mean ± SD) | After treatment (Mean ± SD) |
|---|---|---|
| TG (triglyceride) (mg/dl) | 308 ± 7.5 | 334 ± 118.2 |
| LDL cholesterol (mg/dl) | 95 ± 9.0 | 91 ± 13.6 |
| HDL cholesterol (mg/dl) | 34.5 ± 0.5 | 33 ± 4.0 |

Example 3

(1) Patient

A 59-year-old man with refractory angina. The patient first experienced effort angina at the age of 56 years. The patient had diffuse coronary artery lesions and underwent PCI (stent placement) at Seg 1-2. The LDL cholesterol level of the patient was controlled at a level of about 50 mg/dL with statin medication. However, his angina worsened the following year, and he underwent PCI (stent placement) at Seg 6 and Seg 8. The patient further underwent PCI (stent placement) at Seg 6 due to unstable angina the following year. The patient was referred to our hospital by his primary doctor, diagnosed with idiopathic TGCV, and started on a tricaprin/trisdecanoin diet. The patient received tricaprin/trisdecanoin in a daily dose of 4.5 g for 3 months.

(2) Assessment of Lipid Accumulation in the Coronary Artery

Angiograms of the coronary artery were taken before and 3 months after the start of the tricaprin/trisdecanoin diet. A standard coronary CT angiography was also performed, and the images were color-coded in the same manner as described in Example 1. The images of the designated segment of the coronary artery were subjected to 3D image analysis in the same manner as described in Example 2 to examine changes in lipid accumulation and vascular lumen size in the designated segment.

Figure 4:
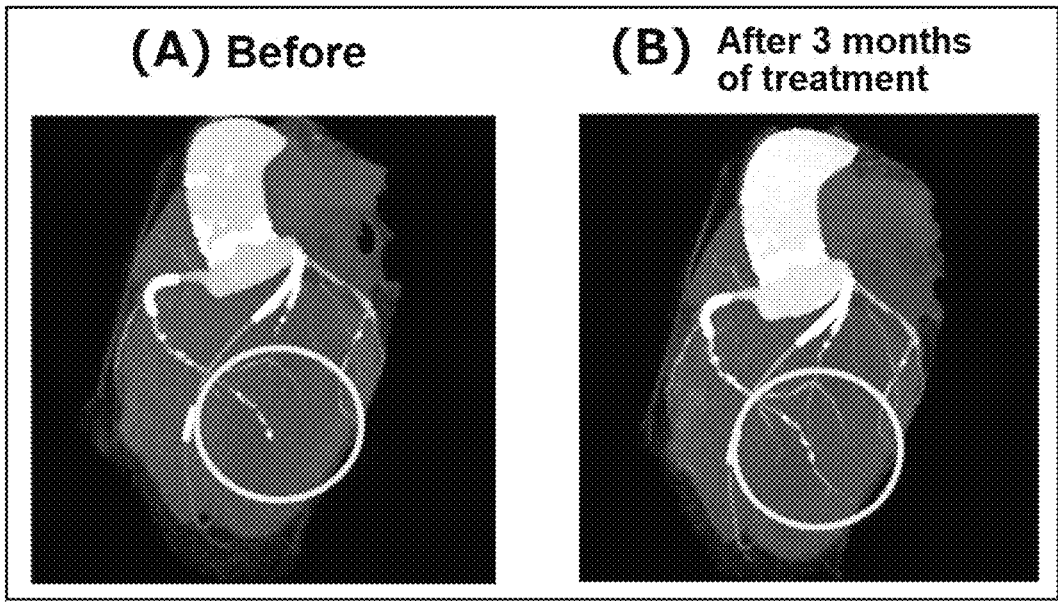
FIG. 4 shows coronary angiograms of the patient in Example 3 before and after a 3-month tricaprin/trisdecanoin diet. The images before the start of the tricaprin/trisdecanoin diet (A) and 3 months after the start of the tricaprin/trisdecanoin diet (B) are shown.
Figure 5:
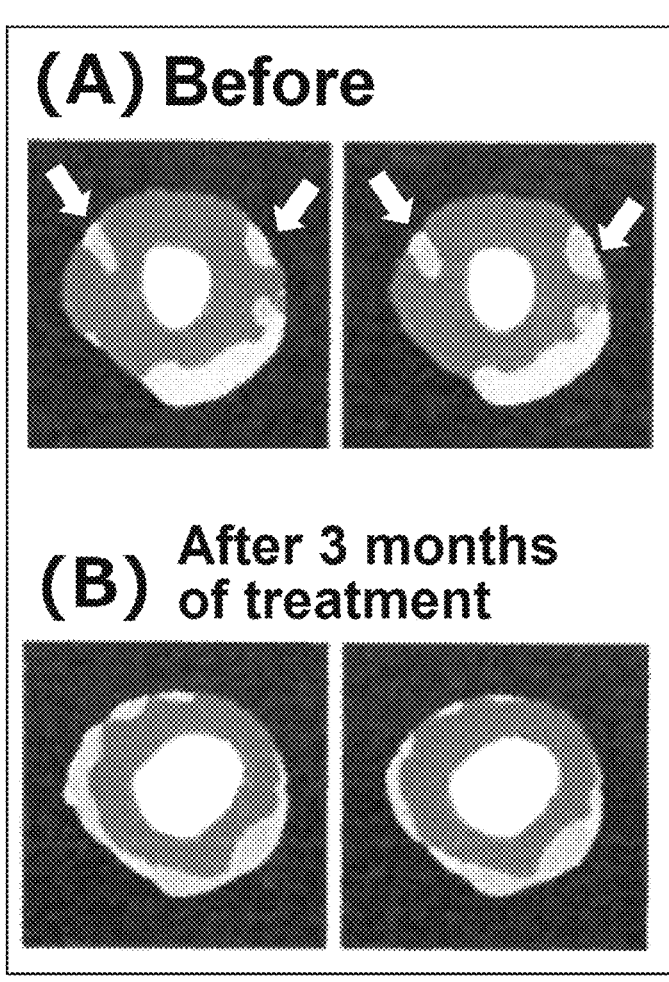
FIG. 5 shows cross-sectional images of the coronary artery in the patient in Example 3 to examine lipid accumulation in the coronary artery before and after a 3-month tricaprin/trisdecanoin diet. The results before the start of the tricaprin/trisdecanoin diet (A) and 3 months after the start of the tricaprin/trisdecanoin diet (B) are shown.

The angiograms of the coronary artery are shown in FIG. 4. The images before the start of the tricaprin/trisdecanoin diet (A) and 3 months after the start of the tricaprin/trisdecanoin diet (B) are shown. In FIG. 4B, the blood flow to the peripheral coronary arteries (vessels in the circled area in the figure) was clearly improved. Color-coded cross-sectional images of the coronary artery are shown in FIG. 5. The images before the start of the tricaprin/trisdecanoin diet (A) and 3 months after the start of the tricaprin/trisdecanoin diet (B) are shown. In FIG. 5A, lipid deposition protruded into the vessel wall from the outside (arrows), resulting in a smaller diameter of the vascular lumen through which the blood flowed, but this was improved in FIG. 5B, showing a normal ring-shaped section of the vessel. The results of the 3D image analysis are shown in Table 3. As shown in FIGS. 4 and 5 and Table 3, the 3-month tricaprin/trisdecanoin diet resulted in regression of TG deposit atherosclerosis in the coronary artery and a marked enlargement of the diameter of the vascular lumen through which the blood flowed, and thus improvement in the blood flow in the coronary arteries as a whole.

TABLE 3

| Segment (not stented) | Lipid accumulation | Vascular lumen |
|---|---|---|
| RCA 3.4 cm | 14% reduction | 24% increase |
| LAD 3.7 cm | 53% reduction | 48% increase |
| Circumflex 7.2 cm | 50% reduction | 17% increase |

RCA: right coronary artery
LAD: left anterior descending coronary artery (3) Changes in Serum Lipid Levels Before and After the Start of the Tricaprin/Trisdecanoin Diet The mean values of the triglyceride, LDL cholesterol, and HDL cholesterol levels measured before the start of the tricaprin/trisdecanoin diet were compared to those measured for 3 months after the start of the tricaprin/trisdecanoin diet. The results are summarized in Table 4. The serum lipid levels after the start of the tricaprin/trisdecanoin diet remained almost unchanged from those before the start of the diet, indicating that tricaprin/trisdecanoin diet had no effect on the serum lipid levels in the patient. The LDL cholesterol level was under control at a level lower than the normal range (60 to 119 mg/dL).

TABLE 4

| Example 3 | Before treatment (Mean ± SD) | After treatment (Mean ± SD) |
|---|---|---|
| TG (triglyceride) (mg/dl) | 78 ± 2.1 | 75 ± 11.3 |
| LDL cholesterol (mg/dl) | 52 ± 2.9 | 54 ± 1.8 |
| HDL cholesterol (mg/dl) | 35 ± 1.0 | 38 ± 1.0 |

Example 4: Effect of Various Fatty Acids on Intracellular Triglyceride Content 4-1 Comparison of Long- and Medium-Chain Fatty Acids A portion of skin tissue was sampled from a diabetic patient after the patient's consent. This sample skin tissue was subjected to primary culture (culture medium: DMEM/ 10% FBS) by a tissue fragment culture method (Explant method) and subsequent successive passages, and then developed into a cell line. The dermal fibroblasts derived from the patient were used to examine the effect of various fatty acids on intracellular triglyceride content. The intracellular triglyceride content of the dermal fibroblasts derived from the diabetic patient was about 5 times higher than the average intracellular triglyceride content of dermal fibroblasts derived from three healthy subjects.

The long-chain fatty acids used were palmitic acid (C16: 0), oleic acid (C18:1), linoleic acid (C16:0), arachidonic acid (C20:4), and eicosatetraenoic acid (C20:5). The medium-chain fatty acids used were heptanoic acid (C7:0) and capric acid (C10:0). These different fatty acids were separately added at 50 μM and 500 μM to the media of dermal fibroblasts from the diabetic patient described above. After 2 days of culture, the cells were collected, and the intracellular triglyceride content was measured using a triglyceride quantification kit (BioVision).

Figure 6:
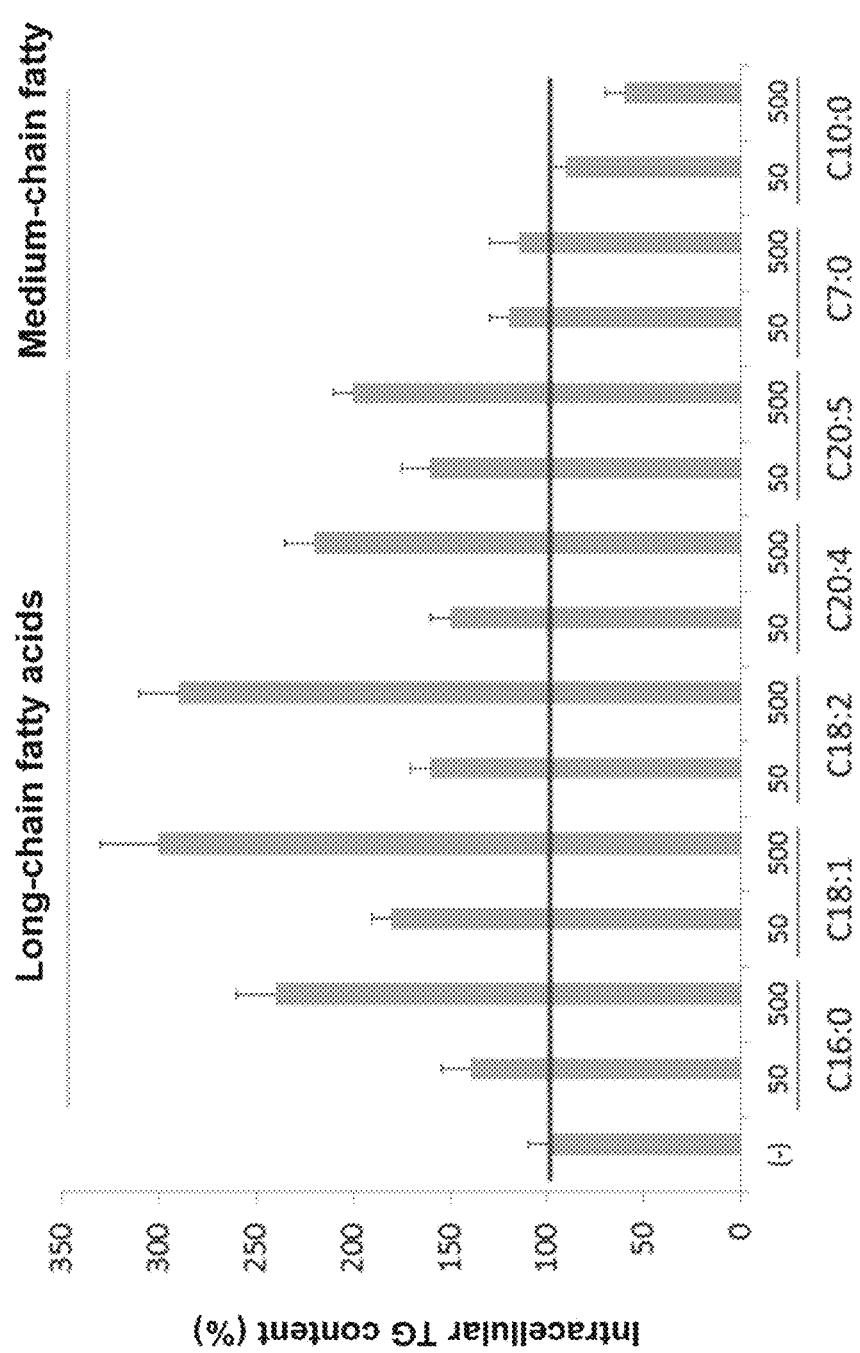
FIG. 6 shows the effect of various fatty acids on the intracellular triglyceride content of dermal fibroblasts derived from a diabetic patient.

The results are shown in FIG. 6. The intracellular triglyceride contents of the cells cultured in the media containing different fatty acids were shown as relative values, assuming that the intracellular triglyceride content of the control cells was 100%. As is clear from FIG. 6, treatment with any of the long-chain fatty acids tested resulted in an increase in intracellular triglyceride content, whereas treatment with a medium-chain fatty acid, capric acid, resulted in a reduction in intracellular triglyceride content.

4-2 Comparison of Various Medium-Chain Fatty Acids

The medium-chain fatty acids used were capric acid (C10:0), caprylic acid (C8:0), and 8-methylnonanoic acid (C8:0). These different fatty acids were separately added at 125 μM and 500 μM to the media of dermal fibroblasts from the diabetic patient described above. After 2 days of culture, the cells were collected, and the intracellular triglyceride content was measured using a triglyceride quantification kit (BioVision). For controls, 500 μM palmitic acid (C16:0) or no fatty acid was added to the medium of the same dermal fibroblasts as those used above.

Figure 7:
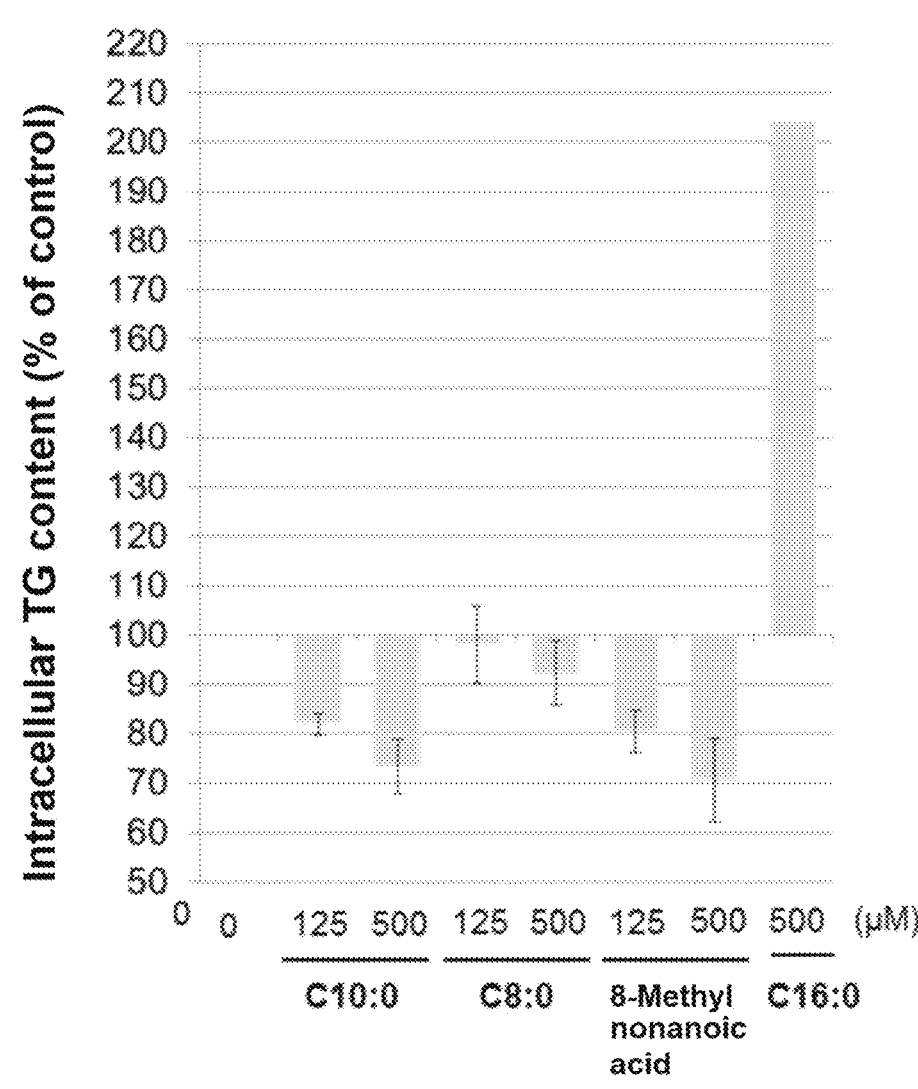
FIG. 7 shows the effect of medium-chain fatty acids on the intracellular triglyceride content of dermal fibroblasts derived from a diabetic patient.

The results are shown in FIG. 7. Treatment with any of the medium-chain fatty acids tested resulted in a reduction in intracellular triglyceride content. Among them, capric acid and 8-methylnonanoic acid were shown to be more potent medium-chain fatty acids for reducing triglyceride than palmitic acid.

The invention claimed is:

1. A method for inducing regression of triglyceride deposit atherosclerosis, comprising administering tricaprin/ trisdecanoin to a patient with triglyceride deposit atherosclerosis, wherein the regression of triglyceride deposit atherosclerosis is accompanied by a reduction of 14% or greater in lipid accumulation and an increase of 17% or greater in vascular lumen in coronary arteries with triglyceride deposit atherosclerosis.

2. The method according to claim 1, wherein the patient with triglyceride deposit atherosclerosis is a patient with refractory atherosclerosis.

3. The method according to claim 1, wherein the patient with triglyceride deposit atherosclerosis is a patient having diabetes or chronic kidney disease, or a patient undergoing hemodialysis.

4. The method according to claim 1, wherein the tricaprin/trisdecanoin is administered in a daily dose containing 1.5 g to 4.5 g for 3 months or more.

5. A method for improving blood flow, comprising administering tricaprin/trisdecanoin to a patient with triglyceride deposit atherosclerosis, wherein the improvement in blood flow is accompanied by a reduction of 14% or greater in lipid accumulation and an increase of 17% or greater in vascular lumen in coronary arteries with triglyceride deposit atherosclerosis.

6. The method according to claim 5, wherein the patient with triglyceride deposit atherosclerosis is a patient with refractory atherosclerosis.

7. The method according to claim 5, wherein the patient with triglyceride deposit atherosclerosis is a patient having diabetes or chronic kidney disease, or a patient undergoing hemodialysis.

8. The method according to claim 5, wherein the tricaprin/trisdecanoin is administered in a daily dose containing 1.5 g to 4.5 g for 3 months or more.

\* \* \* \* \*